United States Patent [19]

Nagase et al.

[11] Patent Number: 5,456,915
[45] Date of Patent: Oct. 10, 1995

[54] COSMETIC COMPOSITIONS

[75] Inventors: Masaaki Nagase, Tokyo; Nahoko Nakashima, Chiba, both of Japan

[73] Assignee: Chesebrough-Pond's USA Co., Greenwich, Conn.

[21] Appl. No.: 40,728

[22] Filed: Mar. 31, 1993

[51] Int. Cl.$^6$ .................................................. A61K 7/48
[52] U.S. Cl. ........................... 424/401; 514/844; 514/847
[58] Field of Search ........................... 424/401; 514/844, 514/847

[56] References Cited

U.S. PATENT DOCUMENTS 4,279,262 7/1981 Horin et al. .................................. 132/7
4,863,725 9/1989 Deckner et al. ........................... 424/81

FOREIGN PATENT DOCUMENTS 0419148 3/1991 European Pat. Off. .
3126811 5/1988 Japan .

*Primary Examiner*—Jyothsna Venkat
*Attorney, Agent, or Firm*—Milton L. Honig

[57] ABSTRACT

A cosmetic composition for increasing the moisture content of skin and/or preventing loss of water from the skin contains a synergistic combination of 1,3-butane diol and 3-methyl-1,3-butane diol as active ingredients.

4 Claims, No Drawings

COSMETIC COMPOSITIONS

This invention relates to cosmetic compositions which have the effect of increasing the moisture content of skin to which they are applied and/or preventing loss of water from the skin. Such compositions are frequently referred to as moisturizing lotions, moisturizing creams, or simply moisturizers.

Many different moisturizers are now available on the market, and they contain a variety of ingredients, amongst which are polyols. A number of polyols are known to be effective as moisturizing agents including glycerol in particular.

The present inventors have found that when two specific polyols are used in combination there is an apparent synergistic effect, giving unexpectedly improved efficacy as moisturizing agent.

Accordingly, the present invention provides a cosmetic composition which contains a combination of 1,3-butane diol and 3-methyl-1,3-butane diol.

1,3-butane diol has the formula:

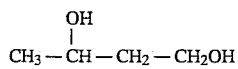

and is also known as 1,3-butylene glycol. One supplier of this material is Kyowa Hakko, Japan.

3-methyl-1,3-butane diol has the formula:

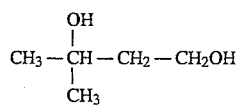

It is available from Kuraray, Japan, under the name "isoprene glycol". This name signifies the route by which it is made, namely the addition of two molecules of water to isoprene.

In places throughout this specification the abbreviation BG will be used to indicate 1,3-butane diol, and the abbreviation IPG will be used to indicate 3-methyl-1,3-butane diol.

A cosmetic composition may contain these materials in amounts ranging from 0.1 to 50% by weight of each, preferably 0.1 to 20%, more preferably at least 0.5% of each. The amounts may be not more than 10% by weight of each. Stated differently, the total amount of these two diols is preferably in the range 0.2 to 50% by weight, more preferred lower limits being 0.5 or 1% by weight and more preferred upper limits being 25 or 40% by weight.

The relative amounts of the two materials will generally lie in a ratio range from 5:1 to 1:5 by weight, preferably 3:1 to 1:3 more specifically 7:3 to 3:7. The ratio of 3-methyl-1,3-butane diol to 1,3-butane diol may possibly lie between 1:1 and 3:7, in particular in the range from 7:13 to 9:11.

A combination of these two polyols may be the sole moisturizing agent in a composition. Preferably, however, other moisturizing ingredients are also included, to yield an even higher moisturizing efficacy.

The inventors have found that certain ingredients are particularly useful in enhancing the moisturizing efficacy of a composition containing a IPG/BG combination. Notably, esters of a monocarboxylic acid having 14 to 20 carbon atoms have been found to be useful in this regard. Specific examples are oleyl oleate, ethyl oleate, glyceryl monooleate, glyceryl dioleate and glyceryl trioleate. Of these, ethyl oleate is particularly preferred. Thus the invention also provides compositions containing the above IPG/BG combination and which further include one or more of these esters.

Other moisturizing ingredients that may be included in the composition are glycerol, urea and sodium hyaluronate.

Other moisturizing ingredients may generally be included in a composition in amounts from 0.1 to 30 or even 50% by weight.

Besides the polyols and other moisturizing ingredients a composition of this invention will be likely to include a cosmetically acceptable vehicle to act as diluent or carrier. The vehicle may be water or a liquid or solid other than water. The balance of any composition may be other cosmetic ingredients and a cosmetically acceptable vehicle.

A composition according to the invention may take the form of a clear isotropic liquid, a cloudy emulsion, a cream or a gel.

Various optional materials may be included, depending on the nature of the composition.

A particularly convenient form of the composition according to the invention is an emulsion, in which case an oil or oily material will normally be present, together with an emulsifier to provide either a water-in-oil emulsion or an oil-in-water emulsion, depending largely on the average hydrophilic-lyophilic balance (HLB) of the emulsifier employed.

Examples of suitable oils include mineral oil and vegetable oils, and oily esters, such as those already referred to above. Other oils or oily materials include silicone oils, both volatile and non-volatile, such as polydimethyl siloxanes.

The oil or oily material, when present for the purposes for forming an emulsion, will normally form up to 90%, preferably from 10 to 80% by volume of the composition.

When a water-in-oil emulsion is required, the chosen emulsifier or emulsifiers should normally have an average HLB value of from 1 to 6. When an oil-in-water emulsion is required, a chosen emulsifier or emulsifiers should have an average HLB value of more than 6.

Other Cosmetic Adjuncts

Examples of conventional adjuncts which can optionally be employed include preservatives, such as para-hydroxy benzoate esters; antioxidants, such as butyl hydroxy toluene; humectants, such as glycerol, sorbitol, 2-pyrrolidone-5-carboxylate, dibutylphthalate, gelatin, polyethylene glycol, preferably PEG 200–600; buffers, such as lactic acid together with a base such as triethanolamine or sodium hydroxide; surfactant such as glycerol ethers; phospholipids; waxes, such as beeswax, ozokerite wax, paraffin wax; plant extracts such as Aloe Vera, cornflower, witch hazel, elderflower, cucumber; thickeners; activity enhancers; colourants; perfumes; and sunscreen materials such as ultrafine titanium dioxide and organic sunscreens such as p-aminobenzoic acid and esters thereof, ethylhexyl p-methoxycinnamate, 2-ethoxyethyl p-methoxycinnamate and butyl methoxydibenzoylmethane, and mixtures thereof.

The composition according to the invention is intended primarily as a product for topical application to human skin, particularly when the skin is dry or damaged, in order to reduce moisture loss and generally to enhance the quality and flexibility of skin. The composition can also be applied to hair and nails.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

EXAMPLES

The following examples include tests to evaluate the moisturizing efficacy of the combination of polyols of this invention, and compared with other polyols. All parts and percentages are by weight unless otherwise stated.

Example 1

In this example the moisturizing efficacy of polyols is evaluated by measuring the rate of evaporation of water from an aqueous solution.

Solutions were prepared containing 50% by weight of a polyol or combination of polyols in deionised water. A control was water without polyol. 5 gm of each aqueous solution was placed in a circular dish having a diameter of 50 mm (so that the surface of the liquid was a 50 mm circle). The dish was then weighed, left to stand at 35° C. and 25% relative humidity, and weighed again to determine the amount of water that had evaporated during that period. The results were expressed as milligram of water evaporating per minute. A low value of water evaporating rate indicates high moisturizing efficacy.

The results are set out in the following Table 1:

TABLE 1

| Polyol (50% aqueous solution) | water evaporating rate (mg/min) |
|---|---|
| 1. None (deionised water control) | 8.0 |
| 2. 1,3-butane diol (BG) | 7.34 |
| 3. 3-methyl-1,3-butane diol (IPG) | 7.13 |
| 4. 3:2 mixture of BG and IPG | 6.68 |
| 5. sorbitol | 7.57 |
| 6. glycerol | 6.9 |

These results in this table show that glycerol was more effective than 1,3-butane diol or 3-methyl-1,3-butane diol when used alone. However, the mixture containing them both in 3:2 ratio gives a lower evaporating rate. (The IPG/BG mixture contained 30% by weight BG and 20% by weight IPG, so as to contain a total of 50% by weight of polyol in water).

Example 2

In this example the moisturizing efficacy of aqueous polyol solutions is evaluated by an in vivo measurement of conductance.

Solutions were prepared containing 50% by weight of polyol, or a combination of polyols, in deionised water. These were tested on human volunteers. A test area of skin which was approximately 2.5 cm by 2.5 cm area of skin in the region of the crook of the elbow was washed with soap and water about 2 hours before the test took place. The subject then rested the arm at conditions equivalent to the evaluation conditions; 20° C. room temperature and 30% relative humidity. A small amount, for example 25 µl, of the sample solution was rubbed into the test area using a circular motion and over a period of about 30 seconds.

Conductance between the probes, applied to the test area at a predetermined spacing, was then measured after 60 minutes. The conductance value will be higher when more moisture is retained in the skin of the test area.

Results are set out in the following Table 2:

TABLE 2

| Polyol (50% aqueous solution) | conductance after 60 minutes (ohm$^{-1}$ × 10$^6$) |
|---|---|
| 1. None (deionised water control) | 40 |
| 2. glycerol | 220 |
| 3. 1,3-butane diol (BG) | 190 |
| 4. 3-methyl-1,3-butane diol (IPG) | 60 |
| 5. 3:2 mixture of BG and IPG | 340 |

Table 2 shows that glycerol gives a higher in vivo moisturizing efficacy than either 1,3-butane diol (BG) or 3-methyl-1,3-butane diol (IPG) alone, but that a combination of these two gives a very much improved in vivo moisturizing efficacy. This unexpectedly high moisturizing efficacy is not to be predicted from the additive effects of BG and IPG and indicates a synergistic effect between the two polyols.

Example 3

In this example, the conductance measurement method described in the preceding example was used to assess moisturizing efficacy of aqueous solutions containing 1% of various fatty acyl esters together with 30% 1,3-butane diol, 20% 3-methyl-1,3-butane diol and 4% nonionic surfactant (polyethylene glycol oleyl ether).

All solutions were made in deionised water. A control omitted the fatty acyl derivative. The procedure was as in the previous example except that the conductance measurement was made after 30 minutes.

Glyceryl monooleate was grade G0901 from Nippon Oils and Fats. Glyceryl dioleate was grade G0902 from Nippon Oils and Fats.

The results are set out in the following Table 3:

TABLE 3

| Fatty acyl derivative (1%) | conductance after 30 minutes 6 (ohm$^{-1}$ × 10$^6$) |
|---|---|
| 1. None (control) | 128 |
| 2. glyceryl monooleate | 168 |
| 3. glyceryl dioleate | 187 |

Table 3 shows that the addition of glyceryl monooleate or glyceryl dioleate to the control sample increases the moisturizing efficacy of the BG/IPG mixture as indicated by the higher conductance values obtained.

Example 4

Further fatty acyl esters were used in the procedure described in the previous example. One solution contained liquid paraffin rather than an ester.

The results are set out in the following Table 4:

TABLE 4

| Additive (1%) | conductance after 30 minutes, (ohm$^{-1}$ × 10$^6$) |
|---|---|
| 1. None (control) | 121 |
| 2. ethyl oleate | 269 |
| 3. oleyl oleate | 199 |
| 4. glyceryl trioleate | 197 |

TABLE 4-continued

| Additive (1%) | conductance after 30 minutes, (ohm$^{-1}$ × 10$^6$) |
|---|---|
| 5. liquid paraffin | 137 |

It can again be seen that addition of an ester to the control solution substantially enhances moisturizing efficacy. All of the esters were supplied by Nippon Oils and Fats. Their designations were:

ethyl oleate EO-P
oleyl oleate OO-P
glyceryl trioleate G903.

Example 5

The in vivo conductance measurement technique described in Example 2 was used to assess four compositions embodying this invention. Some of these compositions contained polyethylene glycol oleyl ether as surfactant. Three such surfactants were used, differing in the average number of ethylene oxide residues in the polyethylene glycol.

The compositions are set out in Table 5 below. Conductance measurements were made as described in Example, except that the measurement was made only 10 minutes after applying the composition.

The results are included in Table 5 below where POE(n) Oleyl ether denotes polyethylene glycol oleyl ether with average n ethylene oxide residues.

TABLE 5

| Ingredient | % by weight in deionised water | | | |
|---|---|---|---|---|
| BG | 9.0 | 9.0 | 9.0 | 9.0 |
| IPG | 6.0 | 6.0 | 6.0 | 6.0 |
| POE (20) oleyl ether | | | | 2.0 |
| POE (10) oleyl ether | | 1.4 | 1.4 | |
| POE (6) oleyl ether | | | 0.8 | 0.8 |
| oleyl alcohol | | | 0.1 | 0.1 |
| ethyl oleate | | | | 1.0 |
| Conductance after 10 minutes (ohm$^{-1}$ × 10$^6$) | 43 | 58 | 158 | 57 |

Example 6

A fully formulated moisturizing lotion has the following formulation:

| Ingredient | weight % |
|---|---|
| polyethylene glycol | 4.5 |

| Ingredient | weight % |
|---|---|
| oleyl ether (average 20EO) | |
| sorbitan monooleate | 0.5 |
| glyceryl trioleate | 20.0 |
| stearyl alcohol | 2.0 |
| 1,3-butane diol (BG) | 3.0 |
| 3-methyl-1,3-butane diol (IPG) | 2.0 |
| methyl parahydroxy benzoate | 0.2 |
| propyl parahydroxy benzoate | 0.1 |
| Carbopol 941 | 0.8 |
| water | balance to 100% |

Carbopol 941 is a cross-linked polyacrylate which acts as a thickener.

Example 7

A moisturizing lotion has the formulation:

| Ingredient | weight % |
|---|---|
| 3-methyl-1,3-butane diol (IPG) | 2.4 |
| 1,3-butane diol | 1.6 |
| glycerol | 1.0 |
| polyethylene glycol decyl ether (average 10EO) | 0.7 |
| polyethylene glycol oleyl ether (average 20EO) | 1.3 |
| ethyl oleate | 0.5 |
| oleyl alcohol | 0.4 |
| citric acid monohydrate | 0.35 |
| disodium hydrogen phosphate | 0.65 |
| methyl paraben (preservative) | 0.1 |
| water | balance to 100% |

We claim:

1. A cosmetic composition comprising a combination of 1,3-butane diol and 3-methyl-1,3-butane diol in a relative ratio of about 3:2 by weight.

2. A cosmetic composition according to claim 1 further comprising from 1 to 25% by weight of an ester of a monocarboxylic acid, the monocarboxylic acid having 14 to 20 carbon atoms.

3. A cosmetic composition according to claim 2 wherein the ester is ethyl oleate.

4. A cosmetic composition according to claim 1 further comprising from 1 to 25% by weight of material selected from the group consisting of glycerol, glycerol monooleate, glycerol dioleate, glycerol trioleate and oleyl oleate.

* * * * *